United States Patent [19]

Zidulka

[11] 4,282,869

[45] Aug. 11, 1981

[54] APPARATUS FOR OXYGEN TREATMENT

[75] Inventor: Arnold Zidulka, Cote St. Luc, Canada

[73] Assignee: Montreal General Hospital Research Inst., Montreal, Canada

[21] Appl. No.: 51,014

[22] Filed: Jun. 22, 1979

[30] Foreign Application Priority Data

Jul. 21, 1979 [CA] Canada .................................. 307887

[51] Int. Cl.³ ............................................ A61M 15/00
[52] U.S. Cl. .......................... 128/200.28; 128/204.25
[58] Field of Search ...................... 128/200.28, 200.27, 128/204.18, 204.25, 200.24, 139, 201.22

[56] References Cited

U.S. PATENT DOCUMENTS

| 1,974,828 | 9/1934 | Markut | 128/200.28 |
| 3,530,515 | 9/1970 | Jacoby | 128/200.24 |
| 3,683,907 | 8/1972 | Cotabish | 128/200.28 |
| 3,736,927 | 6/1973 | Misaqi | 128/201.25 |

FOREIGN PATENT DOCUMENTS

| 545607 | 3/1956 | Belgium | 128/200.28 |
| 1201702 | 7/1959 | France | 128/200.28 |

Primary Examiner—Henry J. Recla

[57] ABSTRACT

An apparatus is provided for supplying a constant predetermined concentration of a predetermined gas at the ingress area of a living body, such as the nose and mouth of a human being, which includes an adjustable support adapted to be fixed to the person's head, and the support mounts a nozzle head. The nozzle head includes a plurality of nozzles spaced about an axis of the nozzle head. The nozzle head is spaced from the nose and mouth area such that ready unimpeded access to the nose and mouth area is obtained. Means are provided for supplying the gas under pressure through the nozzles. The nozzle head and adjustable support means are adapted for adjustment such that the axis of the nozzle head passes through the center of the ingress area formed by the nose and mouth of the person, and each nozzle is projected at a small angle to the axis so as to form a pressurized cone of the gas towards the ingress area of a person.

11 Claims, 4 Drawing Figures

APPARATUS FOR OXYGEN TREATMENT

BACKGROUND OF THE INVENTION

1. Field of the Invention

The present invention relates to an apparatus for supplying a concentration of a gas, and more particularly, to an apparatus for providing a concentration of oxygen at the oxygen ingress area of a living body.

2. Description of the Prior Art

Heretofore, when it is required to provide a human body or animal with a supply of oxygen for breathing, the concentration of which must be higher than the concentration of oxygen in the atmosphere, it has been customary to use a face mask in the case of human beings or a muzzle mask in the case of most four-footed animals. For example, the face mask includes a cup having a cavity normally large enough to cover the nose and mouth areas of a human being and a strap for holding the cup directly against the face of the human being. Of course, a conduit for supplying the concentration of oxygen to the cavity in the cup from the source of the concentration of oxygen is also provided. Muzzle masks are similarly constructed.

In order to eat and drink, however, these socalled oxygen masks must usually be removed during the period of time it takes for the person to ingress the food or drink. While the mask is removed, the person is, of course, breathing ordinary air, with the normal concentration of oxygen in the area of 21% by volume or impure air. In the case of a patient requiring a higher concentration of oxygen at a constant rate, the oxygen mask can be controlled such that, for instance, 24 or 28% of oxygen by volume would normally be supplied. When that patient removes the mask to eat, he would be experiencing an oxygen deficiency for the period of time that the oxygen mask is removed from his or her face. Other problems occur with people who are forced to wear oxygen masks over a prolonged period of time, i.e., the mask provides the illusion of restriction which ironically gives the person a feeling that he is lacking air. In addition, since the rim of the mask is continuously pressing against a person's face, it becomes uncomfortable to wear.

SUMMARY OF THE INVENTION

It is an aim of the present invention to provide apparatus for supplying a constant predetermined concentration of a predetermined gas at the ingress area of a living body, such as the nose and mouth of a human being or muzzle of a four-footed animal.

A further aim of the present invention is to provide an apparatus for supplying a predetermined constant concentration of oxygen in the area of the nose and mouth of a person while avoiding the disadvantages mentioned above in relation to a conventional oxygen mask.

It is a further aim of the present invention to provide an apparatus for supplying a predetermined constant concentration of oxygen in the immediate area of the nose and mouth of a person, yet allowing clear access to the person's nose or mouth thereby allowing the person to eat the food and drink without even temporarily reducing the concentration of oxygen required by the person.

An apparatus in accordance with the present invention includes a nozzle head, an adjustable support adapted to be removably fixed relative to a person's head, the nozzle head including a plurality of nozzles spaced about an axis of the nozzle head, means for supplying the gas under pressure through the nozzles, the nozzle head being spaced from the nose and mouth area such that ready unimpeded access to the nose and mouth area is obtained, said nozzle head and adjustable support means being adapted for adjustment such that the axis of the nozzle head passes through the center of the ingress area formed by the nose and mouth of the person, and each nozzle is projected at a small angle to the axis so as to form a pressurized cone of the gas towards the ingress area of the person.

BRIEF DESCRIPTION OF THE DRAWINGS

Having thus generally described the nature of the invention, reference will now be made to the accompanying drawings, showing by way of illustration, a preferred embodiment thereof, and in which.

DESCRIPTION OF THE PREFERRED EMBODIMENTS

Figure 1:
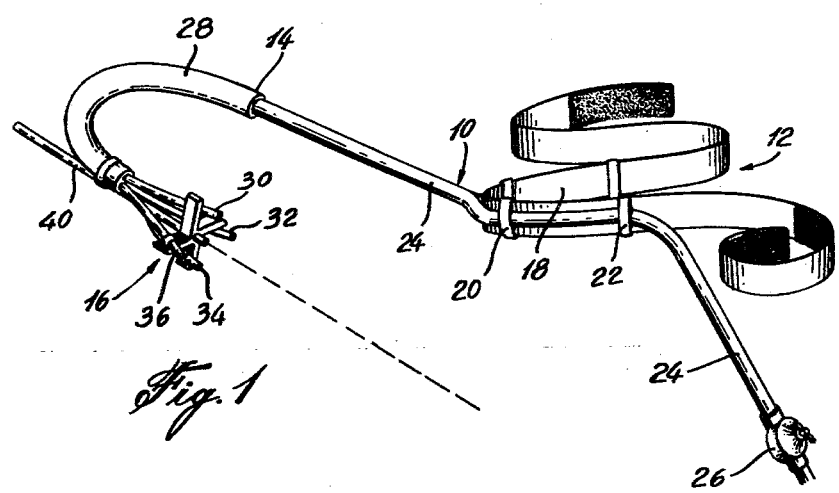
FIG. 1 is a perspective view of the apparatus in accordance with an embodiment of the present invention.
Figure 2:
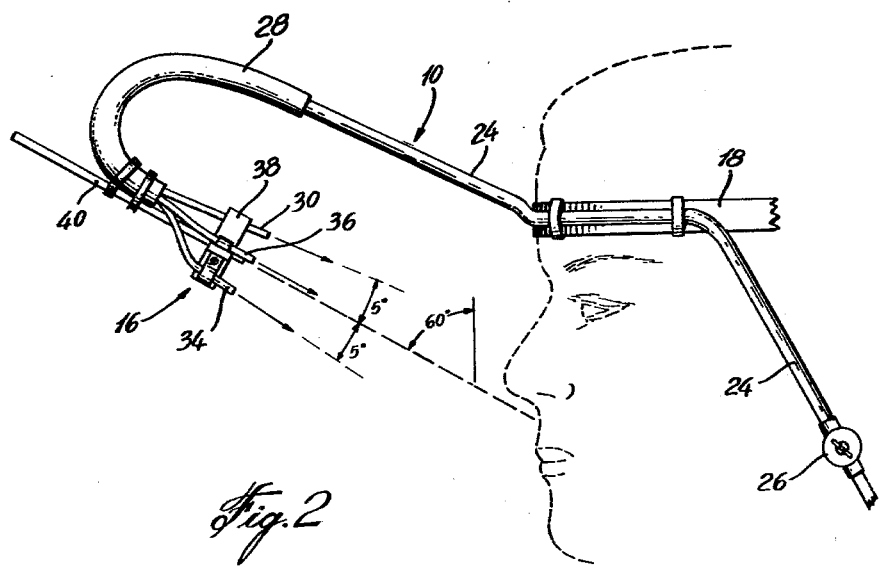
FIG. 2 is a side elevation of the apparatus in a suitable position on a person's head shown in dotted lines.

Referring now to the drawings and especially to FIGS. 1 and 2, there is shown a typical oxygen supply device 10 having head gear 12 to which is mounted an adjustable support member 14 holding at the end thereof a nozzle head 16.

The head gear 12 includes a flexible head band 18 having a size adjustable fastener, such as a fastener known under the trade mark "VELCRO", for adjustably mounting the head gear 12 to the head of a typical person, as illustrated in dotted lines in FIG. 2.

An oxygen supply tube 24 is attached to the head band 18 by means of holding members 20 and 22. In order to properly balance the device, it may be necessary to have a bifurcate tube 24, with one leg of the tube passing on either side of the head band 18. A flow control valve 26 is provided in the tube or tubes 24. A relatively rigid section of the tube 24 extends from the head band at a slight angle upwardly therefrom and communicates with a resilient tube which can be bent, made from various plastics materials or metal, and which holds its form when bent. The tube 28 also acts as a manifold for the four nozzles 30, 32, 34 and 36 which exit therefrom at the other end. The nozzles 30 to 36 make up the nozzle head, and by means of the resilient tube portion 28, are aimed in a reverse direction towards the person's face.

Figure 3:
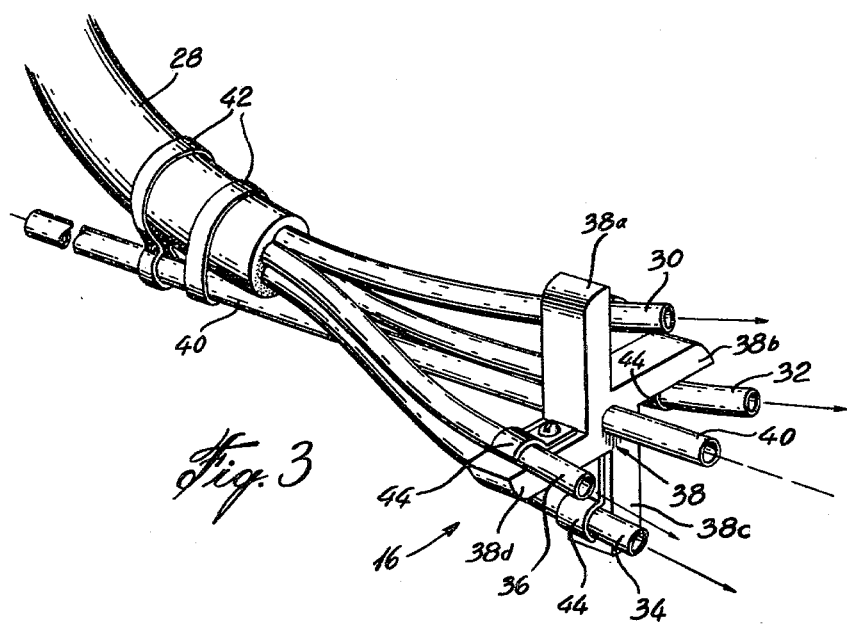
FIG. 3 is an enlarged fragmentary perspective view of a detail of the apparatus.
Figure 4:
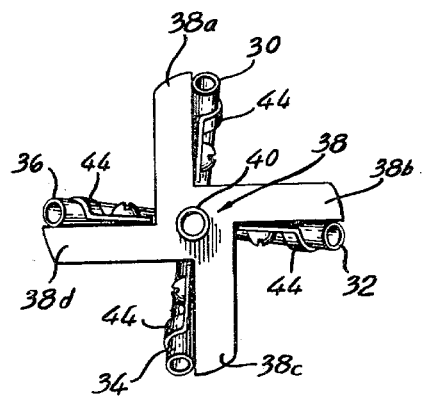
FIG. 4 is a front elevation of the detail shown in FIG. 3.

The nozzle head includes a spacer member 38 having arms 38a, 38b, 38c and 38d, as shown in FIGS. 3 and 4, which is itself mounted to a rigid support member 40 which is generally straight and hollowed out and is concentric with the axis of the nozzle head 16 such that the support member 40 can be used as a sighting tube for aiming the nozzle head 16 at the proper angle towards the nose and mouth of the person carrying the oxygen supply device 10. Each arm 38a, 38b, 38c and 38d, supports a respective catheter 30, 32, 34 and 36, each by means of a simple clamp 44 with one clamp 44 on each arm. Finally, the nozzle head 16 is held in relation to the tube 28 by the rigid support member 40 connected and supported to the tube section 28 by means of holding straps 42.

The above recited structure is but one embodiment and, of course, fewer or more nozzles can be provided in the nozzle head to create the desired effect.

It has been found through experiment that in order to maintain an ultimate controlled constant concentration of oxygen in the nose and mouth area of the person, the axis of the nozzle head 16, represented by the sighting support tube 40, should be aimed at a center point between the nose and mouth of the person wearing the device 10. In order to provide suitable access for eating or for otherwise having access to one's face, it has been found that it is best to hold the nozzle head 16 as well as the tubing above the area of the nose and mouth, aiming the axis of the nozzle head 16 represented by the tube 40 at an angle of approximately 60° to a vertical plane passing through the face. Furthermore, in order to provide suitable access, the nozzle head 16 should be approximately a distance of at least 8 cm. to 16 cm. from the nose and mouth area.

The normal concentration of oxygen in the atmosphere is approximately 21%. It is known that in providing oxygen therapy to certain patients, the concentration of oxygen in the atmosphere immediately surrounding the nose and mouth area should be approximately 24% oxygen or more, depending on the needs. Various tests were conducted with the embodiment described. In each of the tests, the distance of the nozzle head from the nose and mouth area was varied from between 6 cm. to 20 cm., and the most practical range of distances in the tests was found to be between 10 and 12 cm. In order to increase the distance and to maintain a constant controlled concentration of oxygen at the nose and mouth area, it is necessary to increase the diameter of the nozzles (or provide a larger number of nozzles) and to increase the flow rate of the oxygen supply by means of the flow rate control valve 26. In the tests which were carried out, two sizes of catheters were used: the first had an internal diameter of 1.19 mm., and the second set had an internal diameter of 2.11 mm. Each nozzle in both sets was approximately 2 cm. long and was spaced from the central axis a distance of between 1 cm. to 1.5 cm.

The basis of the tests was to determine the effect to the controlled concentration of oxygen at the area of the nose and mouth caused by error in misalignment of the nozzle head. The tests were conducted using a mass spectrometer sampling oxygen at the upper lip. The nozzles of the nozzle head 16 were located in the tests such that they would be aimed at 0° from the axis of the nozzle head or parallel to the axis, 5°, 10° and 15°. Other than the test at 0°, the tests showing the nozzles angled to the axis provides a cone of pressurized oxygen having a greater area in the vicinity of the face than at the nozzle head. The dilution of oxygen increases with the distance from the face and with the larger angle of deviation from the axis of the nozzle head 16. The preferred angle of deviation was found to be 5° from the axis of the nozzle head 16. It was also found with the tests that to obtain an inspired oxygen concentration of 24 to 25% at the nose and mouth, nozzles having an internal diameter of 1.19 mm. were found preferable with the nozzle head 16 at a distance of 10 to 15 cm. from the face. The flow rate was varied from 2 to 12 liters per minute in these tests while the degree of error in aiming the nozzle head was varied from 0° to 15°.

The maximum drop of controlled concentration at the nose and mouth area was found to be no less than 1%.

Tests were also conducted using the second set of nozzles, that is, having an internal diameter of 2.11 mm., varying the distance from 8 to 15 cm., and the angle of the catheters to the axis of the nozzle head 16 was placed at 5°, 10° and 15°. It was found that with a 5°, 10° or 15° error in aiming the nozzle head, an inspired concentration of oxygen of 27 to 28% was maintained at the nose and mouth area with a maximum drop of less than 10°.

Higher concentrations of oxygen can be maintained under controlled conditions by varying the size of the nozzles and probably the number thereof.

I claim:

1. An apparatus for supplying a predetermined concentration of oxygen to the nose and mouth of a person's head, including adjustable support means adapted to be removably fixed to the person's head, nozzle head means, including at least one jet nozzle, and mounted to said support means such that the jet nozzle is directed towards the nose and mouth of a person's head, supply means supported on the support means for supplying the oxygen under pressure to the nozzle head means, means for adjusting the nozzle head means such that the axis of the jet nozzle passes through the breathing ingress area formed by the nose and mouth of the person, flow rate means associated with said supply means for controlling the flow of oxygen from the nozzle head means to form a volume of a predetermined concentration of oxygen at the breathing ingress area of the person, and said nozzle head means being spaced from the support means such that ready unimpeded access to the nose and mouth area is obtained.

2. An apparatus as defined in claim 1, wherein the nozzle head means includes a plurality of jet nozzles spaced apart and concentric with the central axis of the nozzle head means.

3. An apparatus as defined in claim 1, wherein a sight is provided centrally of the nozzle head means coinciding with the central axis thereof for aiming the nozzle head means towards the center of the breathing ingress area of the nose and mouth of the person.

4. An apparatus as defined in claim 1, wherein the adjustable support means is adapted to be removably fixed relative to a person's head and includes a head gear with a head band adapted to be strapped to a person's head, the supply means including a tube leading to the head band, means supporting the tube thereon, the support means for the nozzle head means including a fixed rigid tube communicating with the tube at the head band, and a resilient portion to which the jet nozzles of the nozzle head means are connected and communicating therewith, whereby the nozzle head means can be adjusted in an angular direction relative to the rigid portion of the tube supporting the nozzle head means.

5. An apparatus as defined in claim 1, wherein the central axis of the nozzle head means is at an angle to a plane taken through the center of the breathing ingress area of the person wearing the apparatus.

6. An apparatus as defined in claim 1, wherein the nozzle head means is adustable with respect to said support means such that it is spaced at between 6 to 20 cm. from the nose and mouth area and the jet nozzles are aimed at an angle of at least 5° from the central axis of the nozzle head means.

7. An apparatus as defined in claim 1, wherein the flow rate means includes a gas flow control valve in the supply means.

8. An apparatus as defined in claim 1, wherein the nozzle head means includes a plurality of individual jet nozzles.

9. An apparatus as defined in claim 1, wherein the flow rate means is adjusted and the jet nozzle size is selected, and the distance from the person's nose and mouth area to the nozzle head means is chosen such that the predetermined concentration of oxygen at the nose and mouth area of the person is between 24 and 28%.

10. An apparatus as defined in claim 9, wherein there are provided four jet nozzles included in the nozzle head means, each jet nozzle having an internal diameter of 1.19 mm. and the flow rate means being adjustable between 2 to 12 liters per minute and the distance of the nozzle head means from the nose and mouth area being adjustable between 6 cm. to 20 cm.

11. An apparatus as defined in claim 10, wherein each of the axes of each jet nozzle is directed at an angle of approximately 5° from the central axis of the nozzle head means so as to form a cone-shaped jet such that the pressurized area at the mouth and nose area of the person is greater than the pressurized area at the nozzle head means.

* * * * *